(12) United States Patent
MacKinnon et al.

(10) Patent No.: US 10,872,408 B2
(45) Date of Patent: Dec. 22, 2020

(54) METHOD AND SYSTEM FOR IMAGING AND ANALYSIS OF ANATOMICAL FEATURES

(71) Applicant: ETREAT MEDICAL DIAGNOSTICS INC., Vancouver (CA)

(72) Inventors: Nicholas MacKinnon, Vancouver (CA); Fartash Vasefi, Sherman Oaks, CA (US); Manuka Shanil Gunasekara, Vancouver (CA)

(73) Assignee: ETREAT MEDICAL DIAGNOSTICS INC., Vancouver (CA)

( * ) Notice: Subject to any disclaimer, the term of this patent is extended or adjusted under 35 U.S.C. 154(b) by 92 days.

(21) Appl. No.: 14/702,570

(22) Filed: May 1, 2015

(65) Prior Publication Data

US 2018/0182091 A1 Jun. 28, 2018

Related U.S. Application Data

(60) Provisional application No. 61/988,002, filed on May 2, 2014.

(51) Int. Cl.
*G06T 7/00* (2017.01)
*G06T 5/00* (2006.01)
(Continued)

(52) U.S. Cl.
CPC .......... *G06T 7/0012* (2013.01); *A61B 5/0077* (2013.01); *A61B 5/1071* (2013.01);
(Continued)

(58) Field of Classification Search
CPC ......... G06T 7/0012; G06T 7/62; G06T 7/194; G06T 2207/10024; G06T 2207/10016;
(Continued)

(56) References Cited

U.S. PATENT DOCUMENTS

| 5,924,074 A | * | 7/1999 | Evans | G06F 19/325 705/3 |
| 8,224,064 B1 | * | 7/2012 | Hassebrook | G06T 7/521 382/154 |

(Continued)

OTHER PUBLICATIONS

Levitt et al., "Automation of arthritis measures in hand radiographs", Jul. 1990, SPIE, Medical Imaging IV: Image Processing, vol. 1233, p. 473-480.*

(Continued)

*Primary Examiner* — Vincent Rudolph
*Assistant Examiner* — Timothy Choi
(74) *Attorney, Agent, or Firm* — Oyen Wiggs Green & Mutala LLP

(57) ABSTRACT

A method and system are provided for characterizing a portion of biological tissue. This invention comprises a smartphone and tablet deployable mobile medical application that uses device sensors, internet connectivity and cloud-based image processing to document and analyze physiological characteristics of hand arthritis. The application facilitates image capture and performs image processing that identifies hand fiduciary features and measures hand anatomical features to report and quantify the progress of arthritic disease.

34 Claims, 12 Drawing Sheets

(51) Int. Cl.
| | |
|---|---|
| G06T 7/194 | (2017.01) |
| A61B 5/107 | (2006.01) |
| A61B 5/00 | (2006.01) |
| G06K 9/00 | (2006.01) |
| G16H 30/40 | (2018.01) |
| G16H 50/20 | (2018.01) |
| G06K 9/62 | (2006.01) |
| G06T 7/62 | (2017.01) |

(52) U.S. Cl.
CPC .......... *A61B 5/1079* (2013.01); *A61B 5/4528* (2013.01); *A61B 5/6898* (2013.01); *G06K 9/00375* (2013.01); *G06K 9/00382* (2013.01); *G06K 9/6211* (2013.01); *G06K 9/6223* (2013.01); *G06T 5/006* (2013.01); *G06T 7/194* (2017.01); *G06T 7/62* (2017.01); *G06T 2207/10024* (2013.01); *G06T 2207/30008* (2013.01); *G06T 2207/30088* (2013.01); *G16H 30/40* (2018.01); *G16H 50/20* (2018.01)

(58) Field of Classification Search
CPC . G06T 2207/30004; G06T 2207/30088; G06T 2207/30196; G06T 2207/3008; G06T 5/006; G16H 30/40; A61B 5/1071; A61B 5/1079; A61B 5/4528; G06K 9/6223
See application file for complete search history.

(56) References Cited

U.S. PATENT DOCUMENTS

| | | | | |
|---|---|---|---|---|
| 9,460,557 | B1 | 10/2016 | Tran et al. | |
| 2006/0062448 | A1* | 3/2006 | Hirsch | G06K 9/6217 382/154 |
| 2009/0002517 | A1* | 1/2009 | Yokomitsu | G06K 9/00771 348/223.1 |
| 2014/0300722 | A1* | 10/2014 | Garcia | G06F 3/0482 348/77 |
| 2014/0316242 | A1* | 10/2014 | Musahl | A61B 5/1127 600/407 |
| 2014/0321718 | A1* | 10/2014 | Wabgaonkar | G06K 9/78 382/115 |
| 2017/0053335 | A1 | 2/2017 | Hanscom | |

OTHER PUBLICATIONS

Jagannathan et al., "Perspective Correction Methods for Camera-Based Document Analysis", Aug. 2005, CVIT, Proceedings of First International Workshop on Camera Based Document Analysis and Recognition, Aug. 2005, Seoul, Korea. pp. 148-154.*

Lester, "The Biomechanical Analysis of the Hand in Rheumatoid Arthritis Patients With MCP Arthroplasty", Jan. 2009, University of Birmingham M. Res., p. 1-93. (Year: 2009).*

Hoßbach et al., "Design and analysis of a calibration-method for stereo-optical motion tracking in MRI using a virtual calibration phantom", Mar. 2013, SPIE, Proceedings Medical Imaging, vol. 8668, p. 86682E-1-p. 86682E-7. (Year: 2013).*

Jonsson et al., "The use of digital photographs for diagnosis of hand osteoarthritis", Feb. 2012, BioMed Central, BMC Musculoskeletal Disorders 13:20, p. 1-13 (Year: 2012).*

Levitt et al., "Automation arthritis measures in hand radiographs", Jul. 1990, SPIE, Proc. SPIE 1233, Medical Imaging IV: Image Processing, p. 473-480. (Year: 1990).*

Arthritis: the big picture. The Arthritis Research Campaign, with statistics from the ARC Epidemiology Unit. Derbyshire, UK, Arthritis Research UK, May 1, 2002.

Wittoek, R., Cruyssen, B. V., & Verbruggen, G. (2012). Predictors of functional impairment and pain in erosive osteoarthritis of the interphalangeal joints: comparison with controlled inflammatory arthritis. Arthritis & Rheumatism, 64 (5), May 2012, 1430-1436.

Haugen I. K., Englund M., Aliabadi P., Niu J., Clancy M., Kvien T. K., et al. Prevalence, incidence and progression of hand osteoarthritis in the general population: the Framingham Osteoarthritis Study. Ann Rheum Dis 2011; 70:1581-1586.

Kwok W. Y., Kloppenburg M., Rosendaal F. R., van Meurs J. B., Hofman A., Bierma-Zeinstra S. M. A., Erosive hand osteoarthritis: its prevalence and clinical impact in the general population and symptomatic hand osteoarthritis. Ann Rheum Dis 2011;70:1238-1242.

Dahaghin S, Bierma-Zeinstra S. M. A., Ginai A. Z., Pols H. A., Hazes J. M. W. , Koes B. W. Prevalence and pattern of radiographic hand osteoarthritis and association with pain and disability (the Rotterdam Study). Ann Rheum Dis 2005;64:682-687.

Kellgren, J. H., & Lawrence, J. S. (1957). Radiological assessment of osteo-arthrosis. Ann Rheum Dis (1957), 16(4), 494-502.

Verbruggen G., & Veys, E. M. (1996). Numerical scoring systems for the anatomic evolution of osteoarthritis of the finger joints. Arthritis & Rheumatism,39(2), Feb. 1996, 308-320.

Verbruggen, G., Goemaere, S., & Veys, E. M. (2002). Systems to assess the progression of finger joint osteoarthritis and the effects of disease modifying osteoarthritis drugs. Clinical Rheumatology (2002), 21(3), 231-243.

Jonsson H., Helgadottir G.P., Aspelund T., Sverrisdottir J.E., Eiriksdottir G., Sigurdsson S., Eliasson G.J., Jonsson A., Ingvarsson T., Harris T.B., Launer L., Gudnason V. The use of digital photographs for the diagnosis of hand osteoarthritis: the AGES-Reykjavik study. BMC Musculoskeletal Disorders 2012;13:20.

Akhbardeh, F., Vasefi, F., Tavakolian, K., Bradly, D., and Fazel-Rezai, R., 2015, "Toward Development of Mobile Application for Hand Arthritis Screening," 37th Annual International Conference of the IEEE Engineering in Medicine and Biology Society (EMBC), Milan, Italy, Aug. 25-29, 2015, pp. 7075-7078.

Munia T.T.K., i Haque I.R., Aymond A., MacKinnon N., Farkas D.L., Al-Hashim M., Vasefi F., Fazel-Rezai R. Automatic clustering-based segmentation and plaque localization in psoriasis digital images. In Healthcare Innovations and Point of Care Technologies (HI-POCT), 2017 IEEE Nov. 6, 2017 (pp. 113-116). IEEE.

Felson, D.T., Lawrence, R.C., Dieppe, P.A., Hirsch, R., Helmick, C.G., Jordan, J.M., Kington, R.S., Lane, N.E., Nevitt, M.C., Zhang, Y. and Sowers, M. et al, 2000. Osteoarthritis: New insights. Part 1: the disease and its risk factors. Annals of Internal Medicine, Oct. 17, 2000, 133(8), pp. 635-646.

Altman R., Alarcon G., Appelrouth D., Bloch D., Borenstein D., Brandt K., Brown C., Cooke T.D., Daniel W., Gray R., Greenwald R. et al. The American College of Rheumatology criteria for the classification and reporting of osteoarthritis of the hand. Arthritis & Rheumatism: Official Journal of the American College of Rheumatology. Nov. 1990;33(11):1601-1610.

Amini M., Vasefi F., MacKinnon N. Validation of hand and foot anatomical feature measurements from smartphone images. In Imaging, Manipulation, and Analysis of Biomolecules, Cells, and Tissues XVI Feb. 22, 2018 (vol. 10497, pp. 1049711-1-1049711-12). International Society for Optics and Photonics.

Litwic, A., Edwards, M. H., Dennison, E. M., & Cooper, C. (2013). Epidemiology and burden of osteoarthritis. British Medical Bulletin, 2013; 105; 185-199.

Salaffi, F., Carotti, M., Stancati, A. and Grassi, W., 2003. Radiographic assessment of osteoarthritis: analysis of disease progression. Aging Clinical and Experimental Research 2003, 15(5), pp. 391-404.

Marshall, M., Jonsson, H., Helgadottir, G.P., Nicholls, E., van der Windt, D., Myers, H. and Dziedzic, K., 2014. Reliability of Assessing Hand Osteoarthritis on Digital Photographs and Associations With Radiographic and Clinical Findings. Arthritis Care & Research, 66(6), Jun. 2014, pp. 828-836.

Stern, A.G., Moxley, G., Rao, T.P.S., Disler, D., McDowell, C., Park, M. and Schumacher, H.R., 2004. Utility of digital photographs of the hand for assessing the presence of hand osteoarthritis. OsteoArthritis and Cartilage (2004), 12(5), pp. 360-365.

Arthritis: the big picture. The Arthritis Research Campaign, with statistics from the ARC Epidemiology Unit. Derbyshire, UK.

(56) References Cited

OTHER PUBLICATIONS

Wittoek, R., Cruyssen, B. V., & Verbruggen, G. (2012). Predictors of functional impairment and pain in erosive osteoarthritis of the interphalangeal joints: comparison with controlled inflammatory arthritis. Arthritis & Rheumatism,6(5), 1430-1436.

Haugen IK, Englund M, Aliabadi P, Niu J, Clancy M, Kvien TK, et al. Prevalence, incidence and progression of hand osteoarthritis in the general population: the Framingham Osteoarthritis Study. Ann Rheum Dis 2011; 70:1581e6.

Kwok WY, Kloppenburg M, Rosendaal FR, van Meurs JB, Hofman A, Bierma-Zeinstra SM. Erosive hand osteoarthritis: its prevalence and clinical impact in the general population and symptomatic hand osteoarthritis. Ann Rheum Dis 2011;70:1238e42.

Dahaghin S, Bierma-Zeinstra SM, Ginai AZ, Pols HA, Hazes JM, Koes BW. Prevalence and pattern of radiographic hand osteoarthritis and association with pain and disability (the Rotterdam Study). Ann Rheum Dis 2005;64:682e7.

Kellgren, JH, & Lawrence, JS (1957). Radiological assessment of osteo-arthrosis. Ann Rheum Dis, 16(4), 494-502.

Verbruggen, G. & Veys, E. M. (1996). Numerical scoring systems for the anatomic evolution of osteoarthritis of the finger joints. Arthritis & Rheumatism,39(2), 308-320.

Verbruggen, G., Goemaere, S., & Veys, E. M. (2002). Systems to assess the progression of finger joint osteoarthritis and the effects of disease modifying osteoarthritis drugs. Clinical rheumatology, 21(3), 231-243.

Jonsson H, Helgadottir GP, Aspelund T, Sverrisdottir JE, Eiriksdottir G, Sigurdsson S, Eliasson GJ, Jonsson A, Ingvarsson T, Harris TB, Launer L, Gudnason V. The use of digital photographs for the diagnosis of hand osteoarthritis: the AGES-Reykjavik study. BMC Musculoskelet Disord.2012;14:20.

Akhbardeh, F., Vasefi, F., Tavakolian, K., Bradly, D., and Fazel-Rezai, R., 2015, "Toward Development of Mobile Application for Hand Arthritis Screening," 37th Annual International Conference of the IEEE Engineering in Medicine and Biology Society (EMBC), Milan, Italy, Aug. 25-29, pp. 7075-7078.

Munia TT, i Haque IR, Aymond A, MacKinnon N, Farkas DL, Al-Hashim M, Vasefi F, Fazel-Rezai R. Automatic clustering-based segmentation and plaque localization in psoriasis digital images. InHealthcare Innovations and Point of Care Technologies (HI-POCT), 2017 IEEE Nov. 6, 2017 (pp. 113-116). IEEE.

Felson, D.T., Lawrence, R.C., Dieppe, P.A., Hirsch, R., Helmick, C.G., Jordan, J.M., Kington, R.S., Lane, N.E., Nevitt, M.C., Zhang, Y. and Sowers, M., 2000. Osteoarthritis: new insights. Part 1: the disease and its risk factors. Annals of internal medicine, 133(8), pp. 635-646.

Altman R, Alarcon G, Appelrouth D, Bloch D, Borenstein D, Brandt K, Brown C, Cooke TD, Daniel W, Gray R, Greenwald R. The American College of Rheumatology criteria for the classification and reporting of osteoarthritis of the hand. Arthritis & Rheumatism: Official Journal of the American College of Rheumatology. Nov. 1990;33(11):1601-10.

Amini M, Vasefi F, MacKinnon N. Validation of hand and foot anatomical feature measurements from smartphone images. InImaging, Manipulation, and Analysis of Biomolecules, Cells, and Tissues XVI Feb. 22, 2018 (vol. 10497, p. 1049711). International Society for Optics and Photonics.

Litwic, A., Edwards, M. H., Dennison, E. M., & Cooper, C. (2013). Epidemiology and burden of osteoarthritis. British Medical Bulletin, Ids038.

Salaffi, F., Carotti, M., Stancati, A. and Grassi, W., 2003. Radiographic assessment of osteoarthritis: analysis of disease progression. Aging clinical and experimental research, 15(5), pp. 391-404.

Marshall, M., Jonsson, H., Helgadottir, G.P., Nicholls, E., Windt, D., Myers, H. and Dziedzic, K., 2014. Reliability of Assessing Hand Osteoarthritis on Digital Photographs and Associations With Radiographic and Clinical Findings. Arthritis care & research, 66(6), pp. 828-836.

Stern, A.G., Moxley, G., Rao, T.S., Disler, D., McDowell, C., Park, M. and Schumacher, H.R., 2004. Utility of digital photographs of the hand for assessing the presence of hand osteoarthritis. Osteoarthritis and cartilage, 12(5), pp. 360-365.

* cited by examiner

FIG. 12
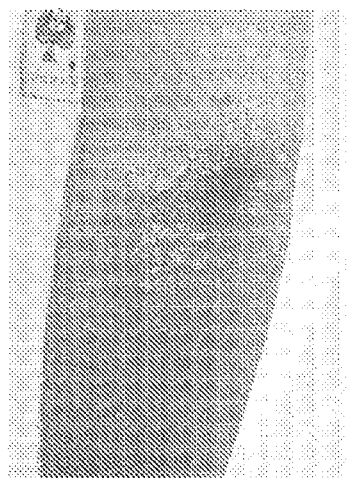
Figure 12a
Figure 12b
Figure 12c

METHOD AND SYSTEM FOR IMAGING AND ANALYSIS OF ANATOMICAL FEATURES

CROSS-REFERENCE TO RELATED APPLICATIONS

Applicants hereby claim the benefit of priority under 35 U.S.C. .sctn.120 to MacKinnon et al. U.S. Provisional Patent Application No. 61/988,002, filed May 2, 2014 and entitled METHOD AND SYSTEM FOR IMAGING AND ANALYSIS OF ARTHRITIS OF THE HAND, the contents of which are hereby incorporated by reference in this disclosure.

FIELD OF THE INVENTION

The present invention relates to methods and systems providing medical equipment for diagnosis, analysis and the monitoring of treatment and detecting, measuring or recording devices for testing the shape, pattern, colour, size of the body or parts thereof, for diagnostic purposes.

BACKGROUND OF THE INVENTION

Arthritis is one of the most common health problems affecting people throughout the world. Hand arthritis primarily affects the articulating joints of the hand and can cause pain, deformity and moderate to severe disability. Hand arthritis is actually many diseases but is grouped into two main types; osteoarthritis (OA) and inflammatory arthritis (IA), (including rheumatoid arthritis). Typical symptoms of hand arthritis are joint swelling and pain. While radiographic features of osteoarthritis are found in 67% of women and 55% of men 55 years and older, symptomatic osteoarthritis is less prevalent.

Recent studies have shown that erosive osteoarthritis of the interphalangeal (IP) joints is an important subset of osteoarthritis because it causes significant functional impairment and pain. While not as severe in terms of pain and disability as inflammatory arthritis, painful erosive osteoarthritis has a greater impact in the general population. One of the common features of symptomatic erosive osteoarthritis is inflammatory episodes in the early course of the disease that result in swelling and tenderness and this condition is sometimes referred to as inflammatory osteoarthritis. This swelling and tenderness manifests in the nerves, blood vessels and supporting matrix that supplies the synovial membrane that encapsulates the joint and produces the synovial fluid that lubricates the joint. It can be assessed by visual observation and palpation, and by quantitative measurements of grip strength.

Many research reports have attempted to quantify and correlate radiographic measurements, functional measurements and patient questionnaires. Treatment remains primarily palliative with very few surgical interventions, such as interphalangeal joint replacement or fusion. Symptomatic rather than radiological presence of osteoarthritis remains the primary indicator of the need for intervention, in most cases by pain control medication.

There have been a number of research initiatives to use optical methods to analyze interphalangeal joint disease including optical coherence tomography, diffuse optical tomography, laser trans-illumination imaging, photoacoustic tomography and digital imaging of both hands and radiographs. In many areas of disease the understanding of the interaction of light and tissue and its application in diagnosis has expanded rapidly. These techniques have historically required specialized equipment for measurement and interpretation.

With the advent of wireless mobile computing devices such as smartphones and tablets this constraint is rapidly changing. Mobile devices are becoming part of the health care ecosystem and applications for smartphones and tablets are proliferating rapidly. The use of imaging and other sensors in smartphone applications is now common and available for the majority of the population in the developed world and many in the developing world.

Coincident with universal deployment of smartphones, is the development and ongoing standardization of the electronic health record as well as the evolution of legislative guarantees of personal access to health records and privacy requirements for agencies transmitting and using electronic health records. These provide ways in which an individual can now have greater autonomy in how they engage with their health providers or payers and have access to their health records. This has also resulted in the evolution of the personal health record services now offered by major telecom and software companies, including Microsoft.

Active patient participation in the management of their disease has been shown to reduce the perceived pain and disability and provide a greater sense of well-being.

It is a goal of this invention to provide individuals who may be developing or have developed arthritis, digital tools to assess and monitor the progress of their disease using their smartphone or tablet as a mobile medical device.

SUMMARY OF THE INVENTION

This invention comprises a smartphone application that allows an individual concerned about or experiencing the symptoms of arthritis to use their smartphone to collect information and to make measurements of their hands. This information can be analyzed to identify changes in the anatomy of the hand that are inconsistent with normal expectations and to track these changes over time. This application is intended to collect sensor data from the smartphone and to analyze and correlate this with biographical information, experiential measures of pain and movement, medication use, weather and regional demographics. It is intended to integrate with existing health record systems compliant with the ISO/IEEE 11073 standards, meet HIPA/HIPAA and other privacy standards and connect to personal health records, like Microsoft Healthvault.

While this invention describes measurement of the hand it will be readily understood that the invention can be used to measure a range of anatomical features including such features as the foot, the leg, the knee, the shoulders or the whole body and any sub feature of an anatomical feature such as a wound, lesion or skin area exhibiting discoloration indicative of a disease or trauma. The body or anatomical feature measured need not be human. For example it could be the body of a mouse, dog or other animal.

The invention comprises a mobile app on a smartphone that collects basic biographical information, captures and calibrates images of the hand, performs anatomical analysis of the calibrated hand image to identify key fiduciary features, make measurements of the hand anatomy and reports and tracks these measurements over time. In some embodiments of the invention the data is transferred and stored on a cloud database server connected wirelessly to the smartphone. In some embodiments of the invention the calibration and analysis of the data is performed by software deployed on a cloud processing server connected to the cloud database server. In some embodiments of the invention the analyzed data and reports are transferred to a personal health record system on a cloud database server. The analysis will identify key features of hand arthritis such as the presence and location of Heberden or Bouchard nodes, angular deviation of the phalanges at the interphalangeal and phalange-metacarpal joints and other characteristic features of osteoarthritis or inflammatory arthritis. Individuals may provide their personal physician, or other health providers, access to this information via their personal health record.

In some embodiments of the invention the invention the method will incorporate biographical and environmental data into the database and analyze these to provide graphical reports of correlations between individual pain, hand appearance, weather, location, age, and gender, and comparison to typical expectations of those who are without symptoms comparable symptoms, etc.

It is to be understood that this summary is provided as a means for generally determining what follows in the drawings and detailed description, and is not intended to limit the scope of the invention. The foregoing and other objects, features, and advantages of the invention will be readily understood upon consideration of the following detailed description taken in conjunction with the accompanying drawings.

BRIEF DESCRIPTION OF THE DRAWINGS

A concise detail of the mechanism of the system is documented below.

FIG. 11a illustrates an image of a hand with the detected boundary overlay.

FIG. 11b illustrates an image of a hand with labeled fingertips and vertices extracted from boundary information. FIG. 11c illustrates an image of a hand with labeled finger centerlines and finger boundary coordinates. FIG. 11d illustrates an image of a hand with labeled finger joint coordinates.

FIG. 12(a)-(c) shows a black and white representation of exemplary color images of an arm showing images of the skin disease psoriasis. FIG. 12a shows an image of the arm with psoriasis following spatial calibration and correction by image warping. FIG. 12b shows the binary image produced by the image segmentation algorithm that separates the psoriatic regions form the normal skin of the arm. FIG. 12c shows an image where boundary detection applied to the binary segmented image is overlaid on the color image of the arm with the psoriatic region.

DEFINITIONS

Figure 1:
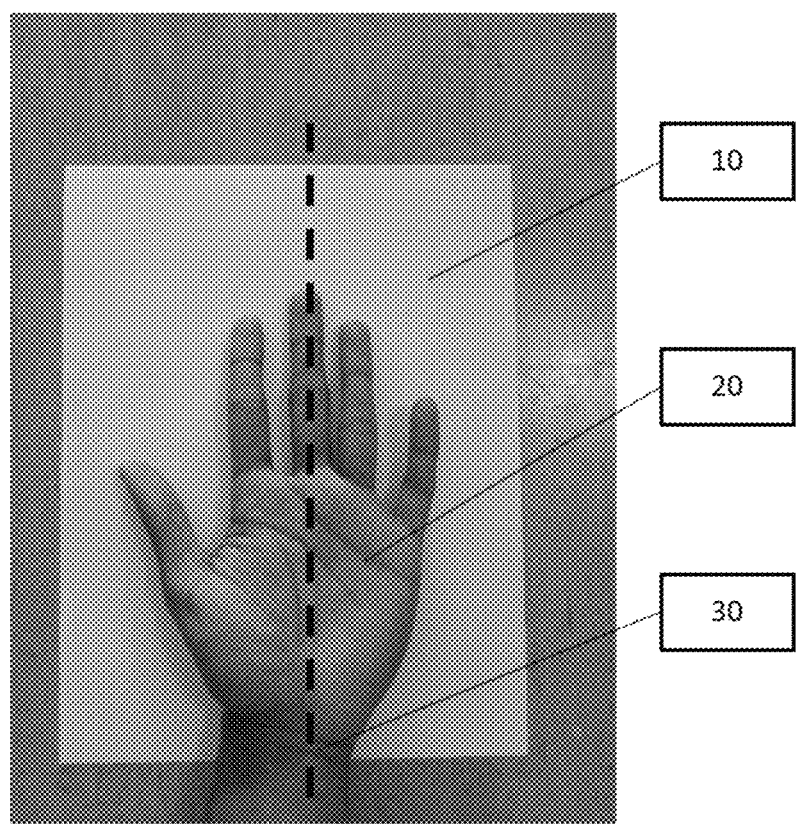
FIG. 1 displays a user-captured image with the desired orientation, field of view and placement of the hand on the surface of a white paper with known dimensions.

The following section provides definitions for terms and processes used in the technical description. A 'Cloud Server' is a virtual private Internet server that enables users to install and run applications, maintain databases and communicate with external input/output devices much like a physical server. It offers flexible, fast outward scalability for operations that is not offered by physical servers.

A 'Cloud Processing Server' is a Cloud Server equipped with sufficiently powerful central processing units (CPUs) and available memory and that functions primarily to process or analyze information, for example, complex image processing.

A 'Cloud Database Server' is a Cloud Server that functions primarily to store and retrieve data that can then be processed, analyzed or reviewed, typically after being transferred to another computer system.

A 'mobile application' is a software application that runs on a mobile platform environment such as Android, Apple iOS or Windows mobile deployed on smart phones and tablets.

An 'electronic health record' is a digital record of patient and physician information that is can be shared across different health care settings.

A 'Hough transform' is a technique that uses voting procedure on parameter space to extract features of an object, in this case long straight lines and lines that form a large blob.

An 'affine transformation' is a geometric transformation that preserves the ratio of distances between points that lie on a straight line. This technique will be used to correct distortion and warping of objects in an image.

'K-means clustering' is a vector quantization method used to cluster observations into groups of related observations.

A 'boundary pixel' is an image pixel that represents an intensity and coordinate on the traced boundary of an object in the image.

A 'Heberden node' is a bony swelling that develops on distal interphalangeal joints.

A 'Bouchard node' is a bony swelling that develops on proximal interphalangeal joints.

A 'fiduciary point' is the representation in image coordinates of anatomical features including fingertips, the vertices between the fingers, the joints of the fingers and similar features.

TECHNICAL DESCRIPTION

The invention comprises a mobile device such as a smart phone or tablet with Internet connectivity, a mobile application installed on the smart phone or tablet and software to process data provided from the smart phone or tablet to the processing software. In a preferred embodiment of the invention, the processing software is installed on a Cloud Server. In another embodiment of the invention, the processing software may be installed on the mobile device. At this time, the processing capability of mobile devices is insufficient to provide sufficient processing capability for some applications. For those applications where the processing capability of the mobile device is sufficient, data processing may occur on the mobile device. In a preferred embodiment of the invention, the method comprises capturing images of the hand using the mobile app on the smart phone and uploading the images to a cloud server for storage and processing.

The invention comprising the mobile device, the mobile application, the cloud data processing server, the cloud data processing software, the cloud database server, the electronic health record software, and the secure communication software is collectively known as the system. The front-end of the system comprises the mobile device and the mobile application, which provides an interface for the user to capture and input images and other data, and provides an interface to review past reports and analyses. The front-end may further comprise a mobile application providing a connection to an electronic health record where user information can be stored.

The back-end of the system comprises the Cloud Processing Server, the data processing software, the Cloud Database Server, and the electronic health record software. The complexity of the data processing software currently requires code structure that cannot be deployed natively on all smart phone environments in a consistent manner. Therefore, it is an advantage of the system to use a Cloud Processing Server to ensure consistency of data processing throughout many mobile platforms and to provide streamlined performance. The Cloud Database Server hosts the electronic health record software and associated databases storing each unique user's data and images, and interfaces with the cloud-processing server. An advantage of deploying both the database and the data processing software on a cloud server ensures that the system operates under a low latency of communication between the data processing server and the database server, providing a faster response time for communicating results to the mobile device. A further advantage of cloud servers is that they provide a deployment environment that is easily scalable for high growth and a secure framework for sensitive patient data.

Turning to the figures, FIG. 1 provides an example of a user taken image that can be processed by the system. A white paper background of known dimensions [10] is placed beneath the hand [20]. The image capture device is oriented so that the orientation of the rectangular paper [10] is approximately the same as that of the image sensor and hence the captured image. Both the paper and hand are preferably within the field of view and the middle finger of the hand is inline with a major axis of the paper [30]. This is the preferred orientation, placement and field of view for image capture and subsequent processing.

Figure 2:
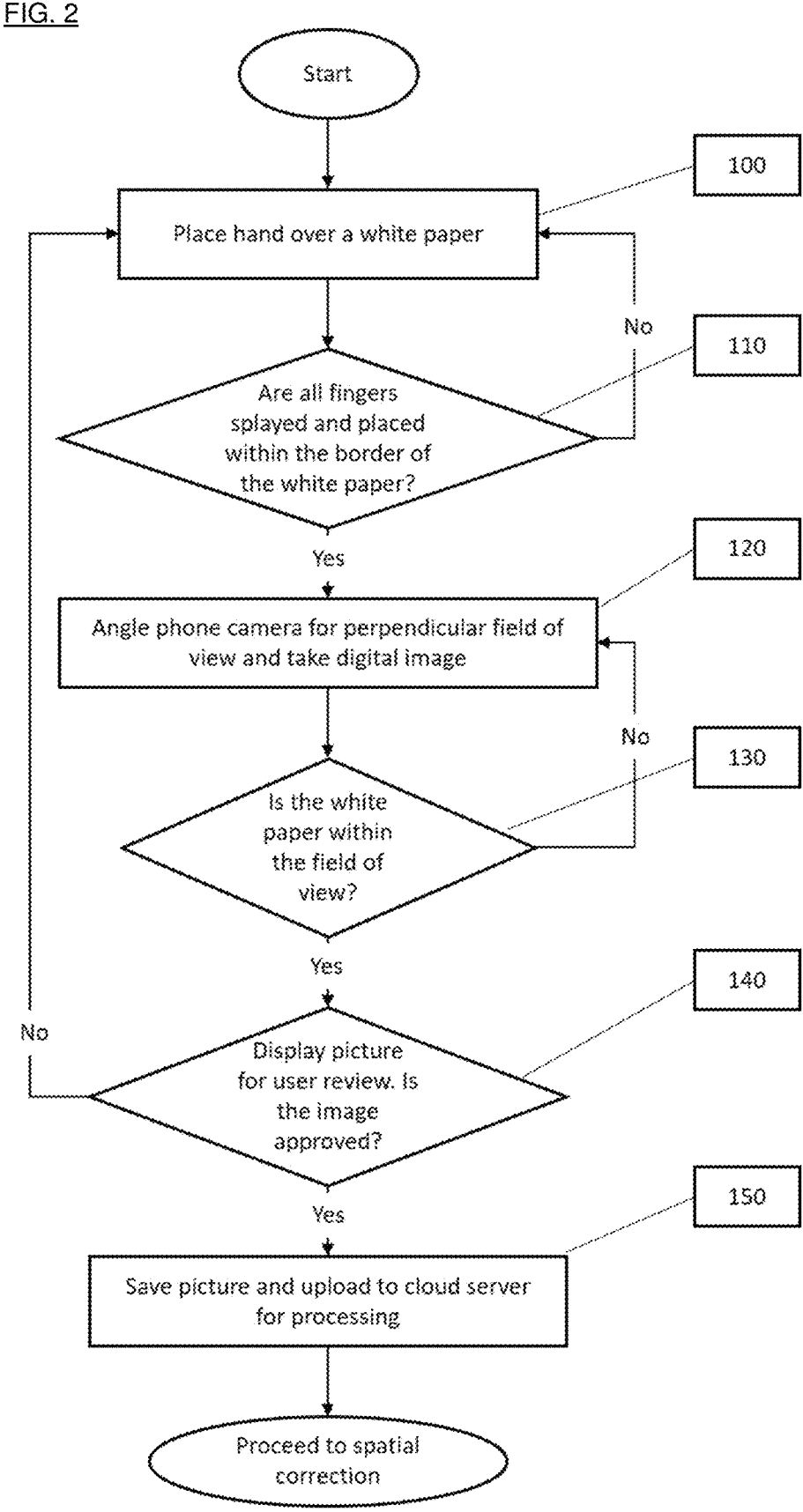
FIG. 2 is a flowchart that describes a preferred method for image-capture.

FIG. 2 shows a flowchart (flowchart 1) that describes the steps taken by the user during this image capture process. The white paper is positioned below the hand [100]. The white paper aids the image segmentation process by serving as a reference object with known dimensions that helps calibrate the spatial features of the image, and as a reference object with a known color response to calibrate the color of the image. All fingers of the hand must be splayed and placed flat within the bounds of the paper [110]. Both the hand and the paper must be within the field of view of the camera [130]. The mobile application provides instructions to the user, guiding the user to orient the device until the camera is reasonably close to perpendicular to the middle finger axis of the hand and to the surface on which the hand is resting to minimize spatial distortion [120]. After capturing the image, the application imports the image for user review and approval [140] and then uploads it to the cloud server for processing [150]. If the image is not approved, the user can retake the image. Possible reasons for not approving the images are image blur due to movement, poor focus or poor brightness and contrast.

Figure 3:
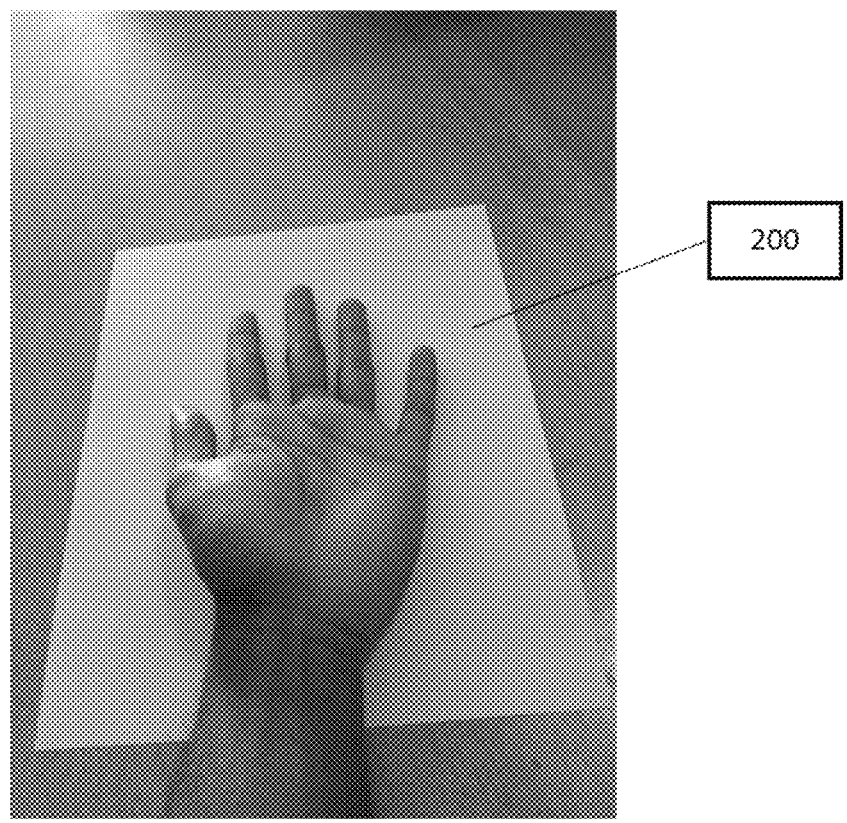
FIG. 3 displays a user-captured image with an undesired orientation where the hand and paper are at an extremely oblique angle.

FIG. 3 illustrates a problem associated with imaging, where an image is captured at an angle too oblique for processing [200]. The data processing software further comprises a calibration method that can correct for moderate orientation errors.

Figure 4:
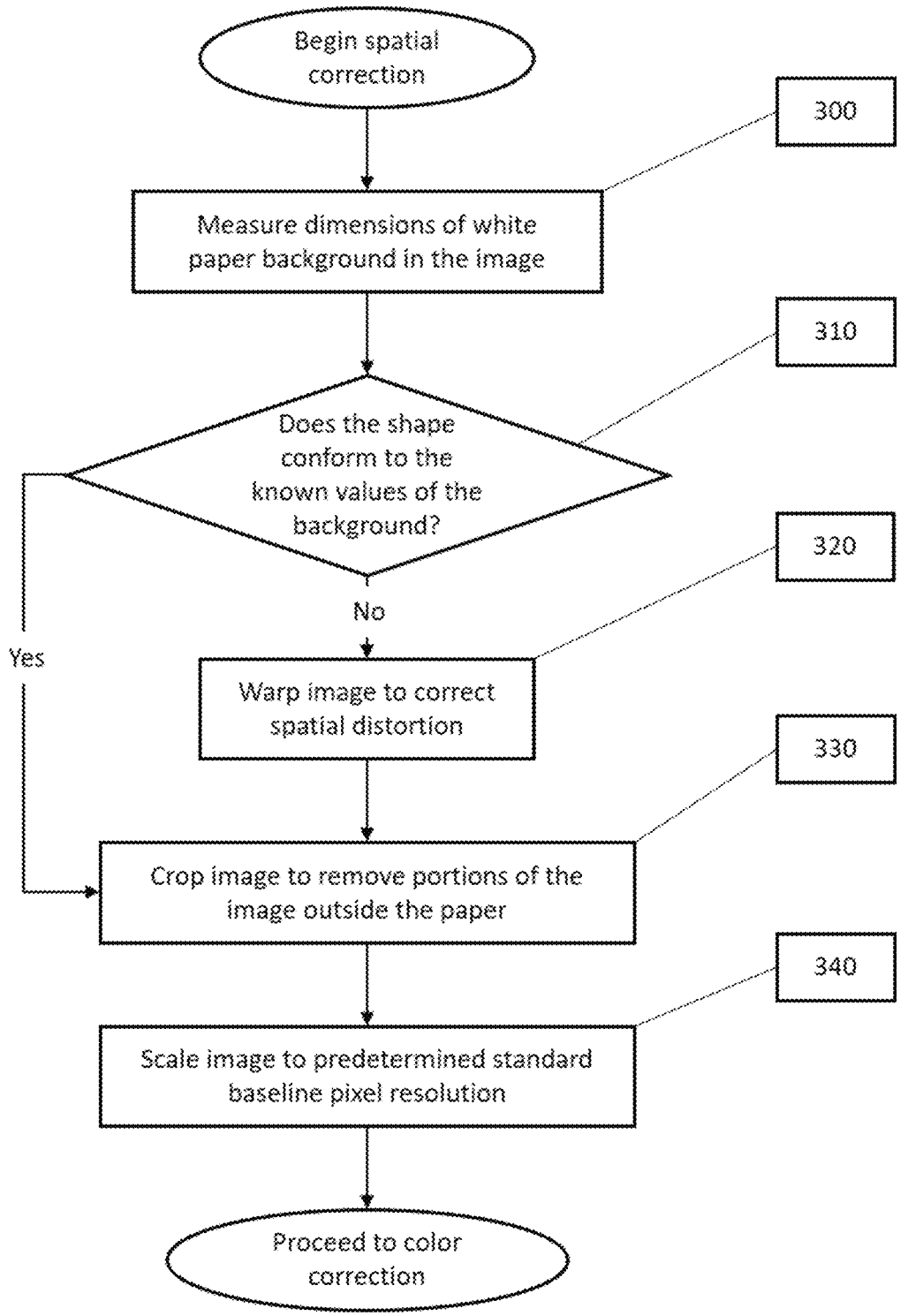
FIG. 4 is a flowchart that describes a preferred method for spatial correction and calibration of images.

FIG. 4 (Flowchart 2) describes a preferred method used by the system to perform spatial correction of moderate orientation errors on the image as well as spatially calibrating the image in real world units such as millimeters or inches. A geometric algorithm [300] measures the dimensions of the representation of the paper object [10] in the image. A preferred algorithm incorporates the Hough transform to identify straight lines in the image typically corresponding to the edges of the paper object placed behind the hand. The intersection points of the straight lines are determined and used to define the coordinates of the corners of the representation of the paper object in the image. From the corners of the representation of the paper object in the image, the measured dimensions of the representation of the paper object in the image are determined. A comparison algorithm [310] evaluates the difference between the measured values of the representation of the paper object in the image and the known dimensions of the paper object. If the measured values do not correspond closely in ratio to the ratios of the known dimensions, then the image is identified as distorted. The calculable difference between measured and known dimensions are used to correct the distortion of the image, a process commonly called warping the image [320]. A preferred method of warping uses an affine transform. The known dimensions of the paper and the measured values from the image are input to an affine transform matrix. The affine transform stretches all points in the image of the paper object until the dimensions of the object are proportional to the known values of the paper object. The image is then cropped and the portions of the image outside of the paper object are removed [330] leaving only the correctly scaled image of the hand and the paper object. The image is then scaled to a predetermined pixel resolution to provide a standard baseline resolution image for further image analysis [340]. In a preferred method, the pixels of the paper object correspond to real world dimensions. An example of this would be making one pixel equal to one millimeter or making one pixel equal to 0.01 inch.

Figure 5:
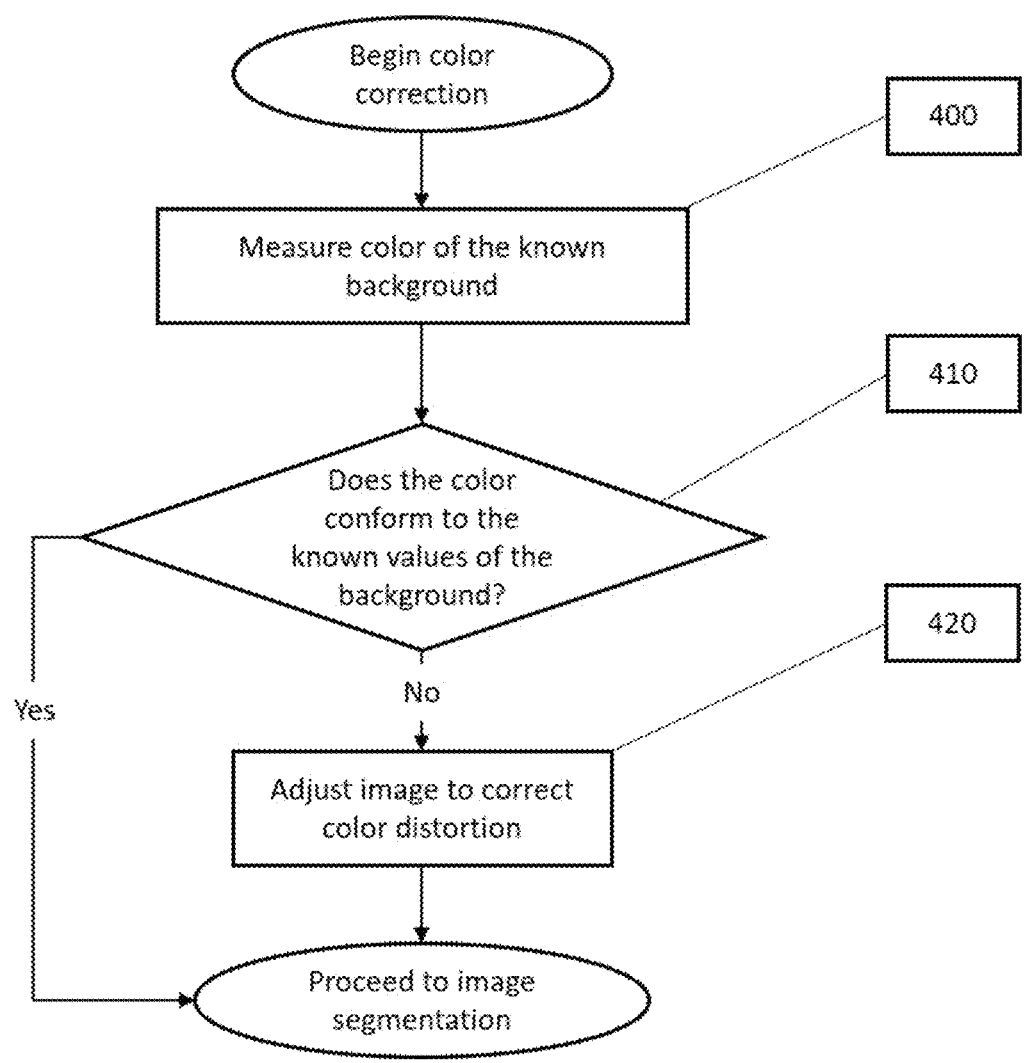
FIG. 5 is a flowchart that describes a preferred method for color correction of images.

FIG. 5 (Flowchart 3) describes a preferred method used by the system to perform color correction on the image. This process is commonly known as white balancing the image. White balancing can be applied to images in different color encoding formats such as Red, Green, Blue (RGB) images, Hue, Saturation, Value (HSV) images, or Luminance, chrominance a, chrominance b (L*a*b) images. An analysis function [400] extracts color values from a portion of the image known to be white paper, determines the deviation of the color values from the known color values and then scales the color values of the image to correct the color of the image. While the details of the image processing required are different for the different color encoding formats, they are well known in the art, accomplish similar results and any form of white balancing can comprise part of the method. A comparison algorithm [410] evaluates the difference between the measured color value of the paper object in the image and the known color value of the paper object. If the color values do not correspond closely, then a color correction function is performed on the image to make the paper object conform to the known values [420]. The program then proceeds to the image segmentation phase.

Figure 6:
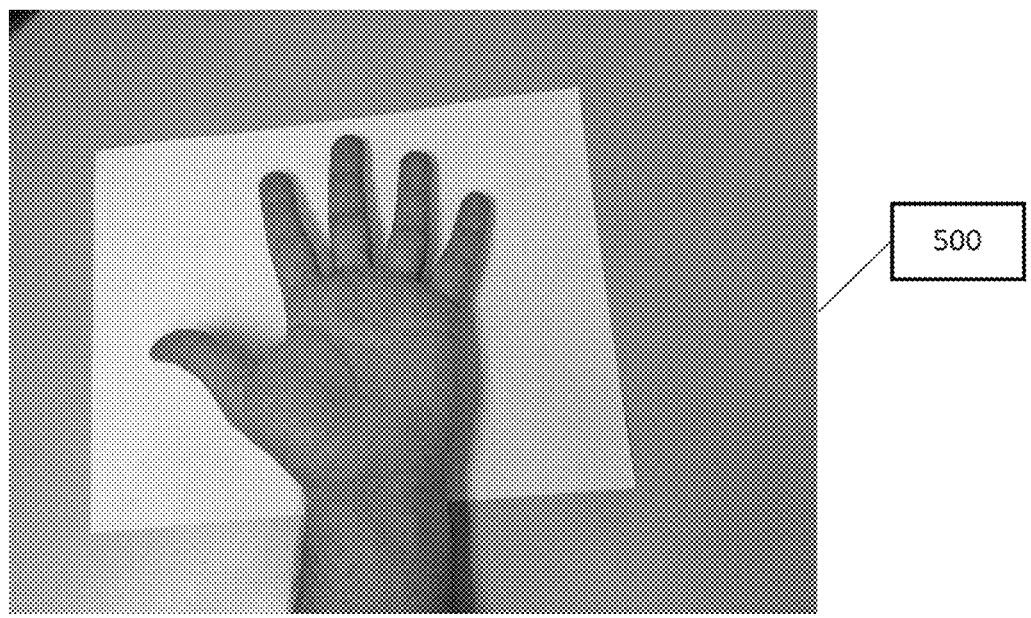
FIG. 6 shows exemplary images of an image being processed to correct for spatial distortion and white balancing.
Figure 6:
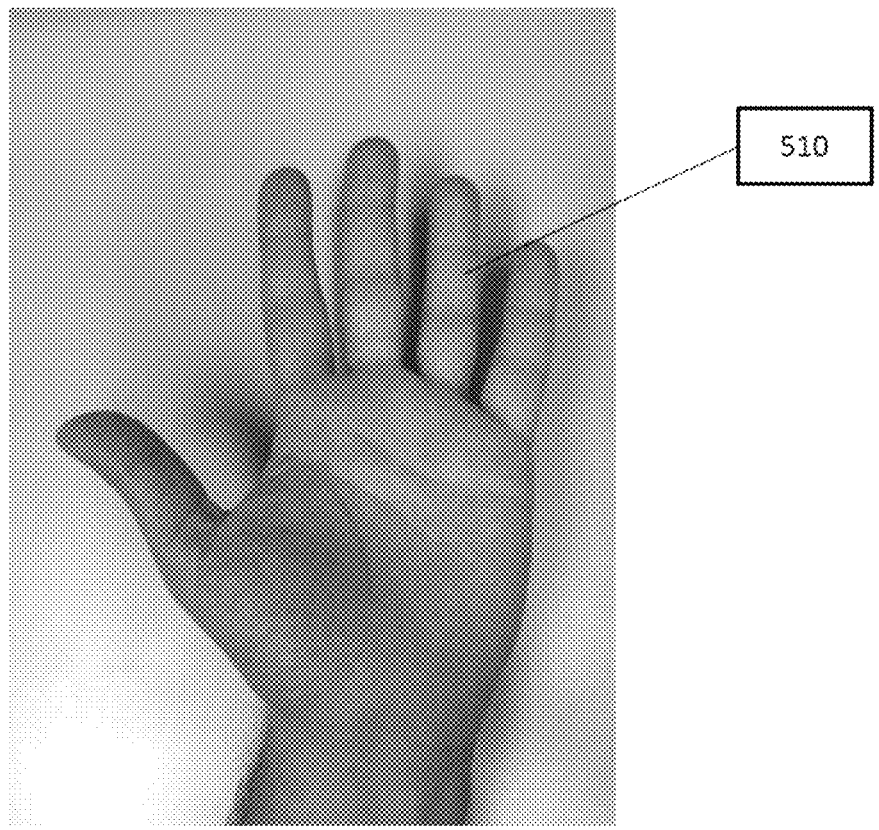

FIG. 6 shows exemplary images exhibiting a user-captured image [500] being cropped processed to correct for spatial distortion and white balancing [510].

Figure 7:
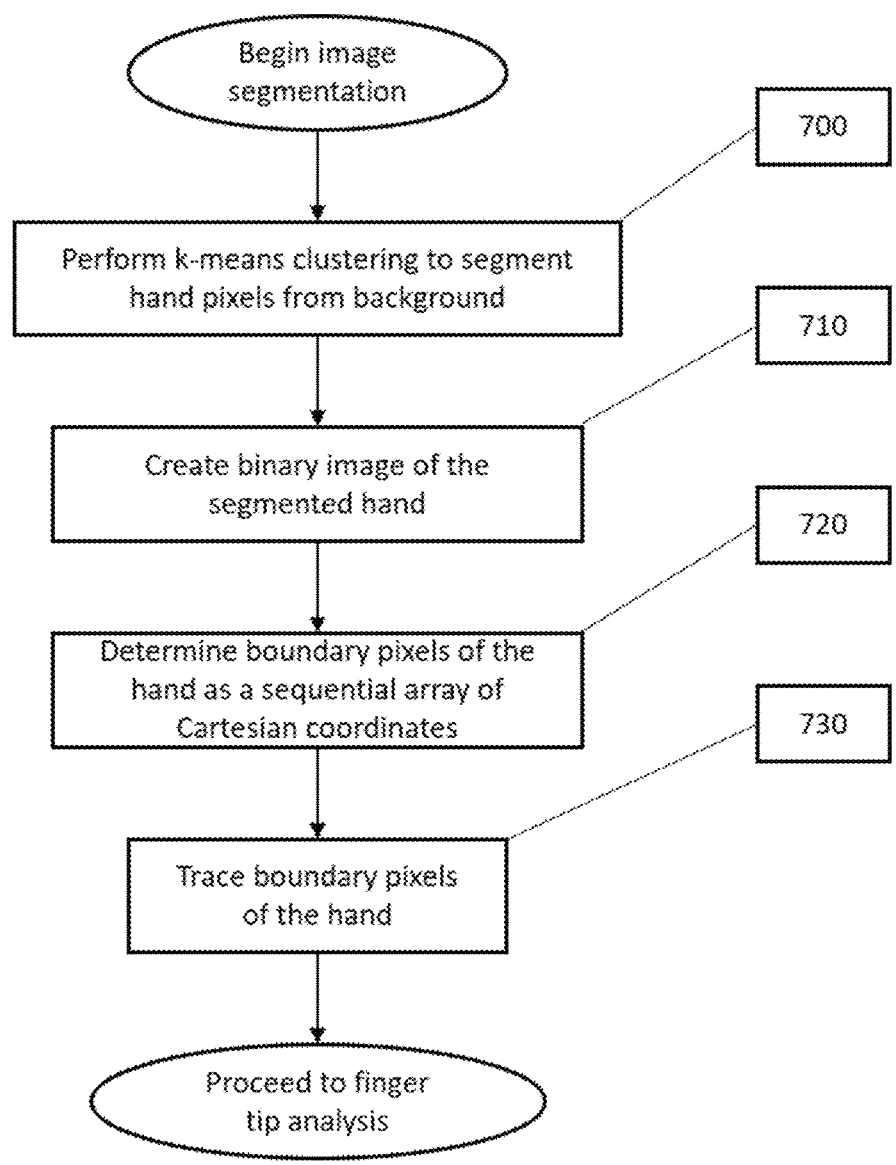
FIG. 7 is a flowchart that describes a preferred method for image segmentation.

FIG. 7 (Flowchart 4) describes a preferred method used by the system to perform image segmentation, separating the portion of the image representing the hand [20] from the remainder of the image. Image segmentation is the separation of features of interest in the image from the rest of the image. A preferred method of image segmentation comprises conversion of the image to a luminance, chrominance color space such as the L*a*b color space. K-means clustering is performed on the *a, *b values of the image [700]. Because there are only two major clusters of color in the image, the chrominance values representing the white paper can be easily separated from the chrominance values representing the hand. A binary image comprising the segmented chrominance values is created for fiduciary analysis [710]. The binary image is analogous to a silhouette image of the hand and clearly outlines the shape of the hand and the fingers. The method further comprises analyzing the binary image of the hand using a boundary function. The boundary function locates the connected components that define the boundary of the hand and order them as a sequential array, of Cartesian coordinates called the boundary array [720] suitable for analysis to determine the location of anatomical fiduciary points such as fingertips, finger vertexes, joints or any other useful anatomical features. The boundary pixels can be represented in pseudo-color to provide a visual report of the boundary as determined by the method [730].

Figure 8:
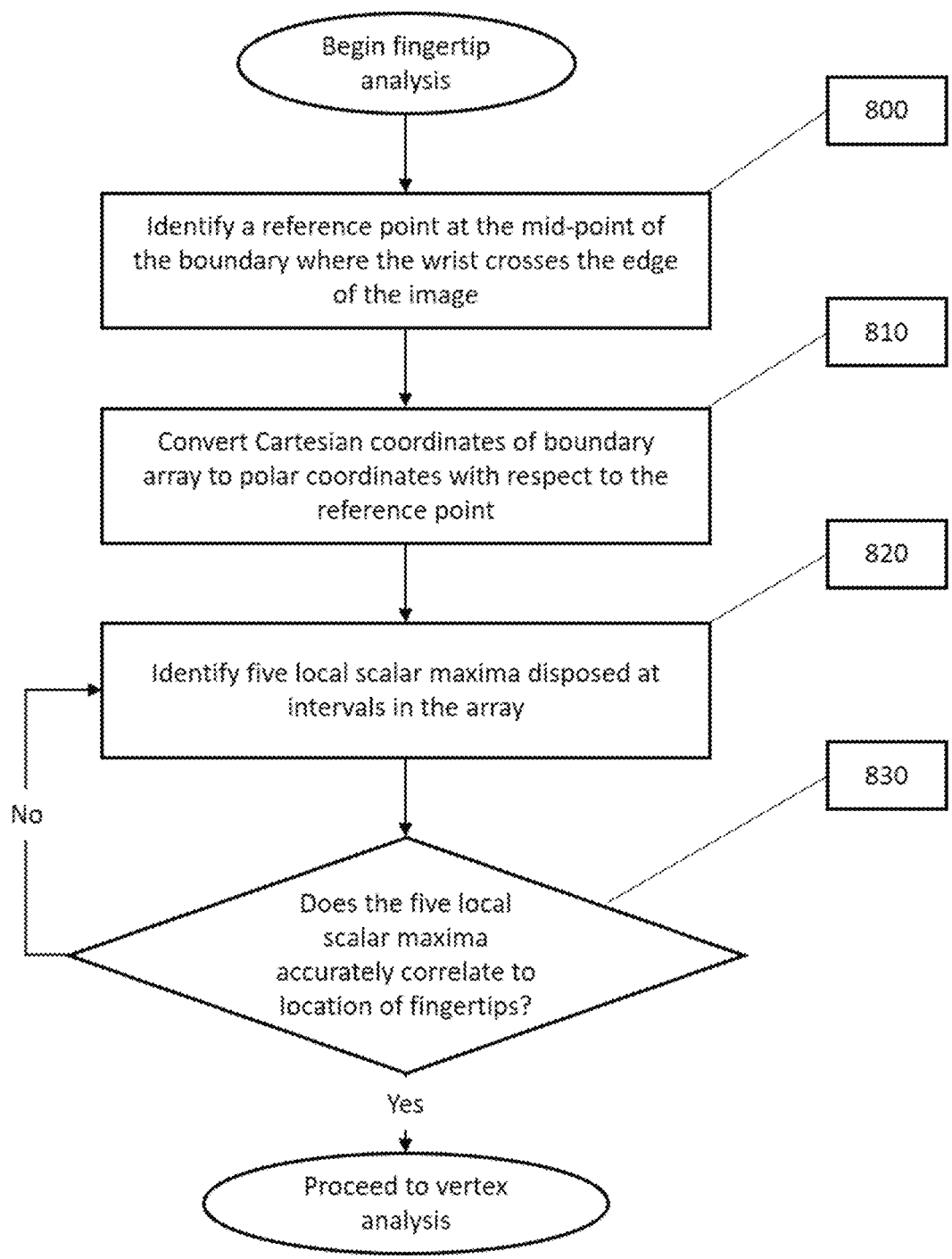
FIG. 8 is a flowchart that describes a preferred method for fingertip analysis.

FIG. 8 (Flowchart 5) describes a preferred method used by the system to identify the fingertips of the hand in the image. The program analyzes the boundary array to determine a reference point. This reference point is located at the mid-point of the boundary where the wrist crosses the edge of the image [800]. The Cartesian coordinates of the boundary array are converted to polar coordinates with respect to the reference point [810]. The polar coordinate for each point of the boundary array comprises an angle and a distance, or scalar value, relative to the reference point. The polar coordinate boundary array is analyzed to identify five local values where the distance is maximal [820]. These five local values where the distance is maximal typically will correspond to the most distant anatomical features, the tips of the fingers and thumb. A preferred method of referencing the fingers and thumbs is to define the thumb as finger 1, the finger adjacent to the thumb as finger 2, the middle finger as finger 3, the finger adjacent to the middle finger but distal with respect to the thumb as finger 4, and the finger most distal from the thumb as finger 5. A minimum interval between each maximum is defined to prevent points along the boundary but near the local maximum for one finger being interpreted as another local maximum. The method then compares the values of the five local scalar maxima to expected values of biologically plausible locations of fingertips [830]. Once the fingertips are successfully identified and labeled, the program proceeds to the finger vertex analysis phase.

Figure 9:
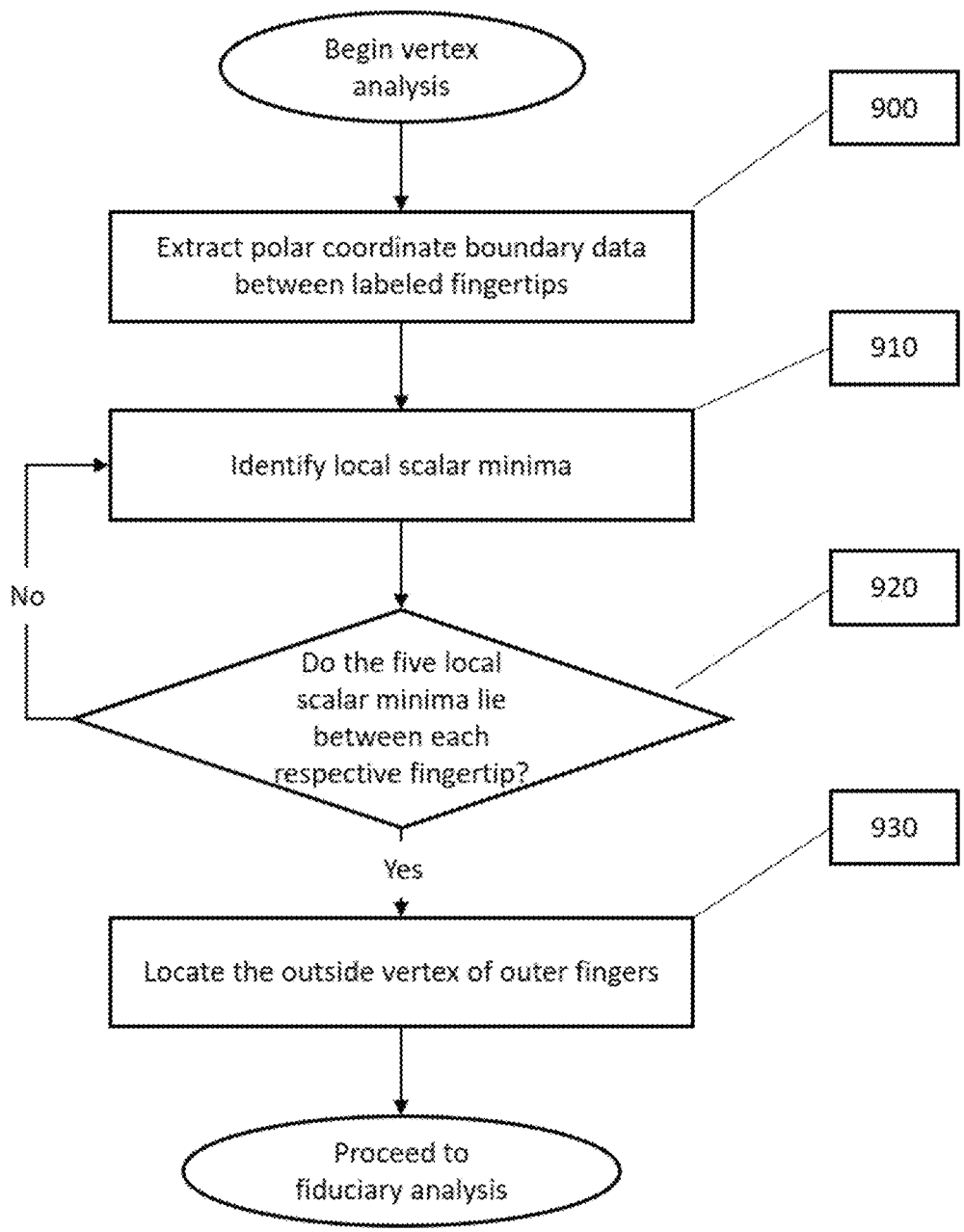
FIG. 9 is a flowchart that describes a preferred method for finger vertex analysis.

FIG. 9 (Flowchart 6) describes a preferred method used by the system to identify vertices between fingers of the hand in the image. The vertices are the points between the fingers that are approximately equidistant from the tips of the fingers and that have a local minimal distance or scalar value with respect to the reference point. In a preferred method, the vertices between fingers 1, 2, 3, 4 and 5 are first determined. The vertices are determined by extracting polar coordinate boundary data between labelled fingertips [900] and analyzing the portion of the boundary array between the tips of adjacent fingers to identify the minimum distance or scalar value with respect to the reference point. Four local minima are located [910] and compared to biologically plausible locations of finger vertices to see if they are valid [920]. This method provides biologically plausible values for the three vertices between fingers 2, 3, 4 and 5 and a biologically plausible vertex that corresponds to the base of finger 1, between finger 1 and 2. The method then turns to the calculation of biologically plausible vertices defining the outermost vertex for finger 1, the outermost vertex for finger 2 and the outermost vertex for finger 5 [930]. Because these values do not correspond to local minima, a different method determining them is used. For finger 1, a distance in terms of index value along the boundary array, between the tip of finger 1 and the local minimum between finger 1 and 2 is determined. A point along the boundary array equidistant in terms of the index value but in opposite direction from the tip of finger 1 is used to identify a point along the boundary array corresponding to the outside vertex of finger 1. The same method is used to calculate the outside vertex of finger 2 and outside vertex of finger 5. Once the vertices are successfully labeled, the program proceeds to the anatomical measurement phase.

Figure 10:
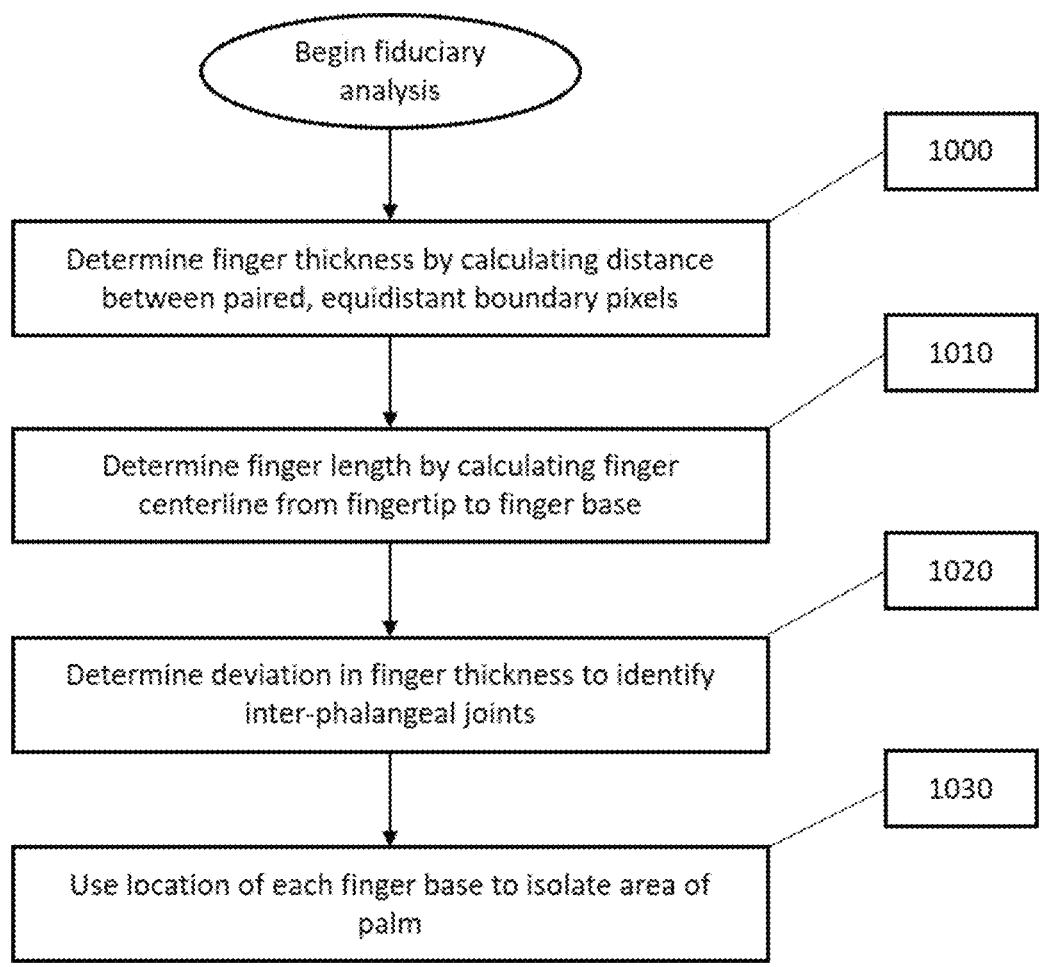
FIG. 10 is a flowchart that describes a preferred method for identifying and measuring the dimensions, location and orientation of fiduciary points of the hand.

FIG. 10 (Flowchart 7) describes a preferred method used by the system to analyze the image of the hand by identifying additional fiduciary points and measuring the dimensions, location and orientation of anatomical features. In a preferred embodiment of the invention, the thickness of each finger is determined. The thickness is determined by identifying pairs of boundary pixels equidistant in index value from the tip of each finger and between the tip of the finger and the vertex [1000]. The distance in millimeters between each pair of pixels is determined, defining the width of the finger at various points along the finger boundary. If desired, the interval in index value between each pair of boundary pixels can be adjusted to speed calculation or reduce the amount of data that needs to be stored. For example, the width of the finger could be determined every 20 pixels along the boundary. Each pair of boundary pixels is also used to determine the centerline of the finger. An array of pixel values corresponding to the midpoint between each pair of boundary pixels defines the centerline of the finger. The length of the finger is determined by measuring the length, in millimeters, of the centerline [1010]. Variation in finger thickness along the centerline can be analyzed to identify and label the interphalangeal joints [1020]. The width of the finger at the joints and other locations can be compared to normal physiological values to identify pathological changes that may indicate the presence of osteoarthritis, rheumatoid arthritis, or other disorders. For example, the ratio of the width of the fingers and the joints can be compared to the width of the finger between the joints to provide an index of the degree of swelling due to inflammation. The finger centerline can be analyzed in segments to determine the length of the finger segment between the interphalangeal joints. The lengths of these segments can be compared to expected physiological parameters to provide an index of finger curling or other indications useful for diagnosis. The angle of the centerline of each segment of a finger can be compared to the angles of the other segments of the finger to provide a diagnostically useful measure of joint breakdown causing deviation from the normal finger axis. A preferred method of analyzing the angle of a finger segment or phalange comprises determining a best linear fit through the data points of a finger centerline segment and determining the deviation of the angle from the expected values for a normal hand. The angle of the centerline for each whole finger can also be used and determined using a best linear fit for the whole centerline of the finger and the angle of orientation relative to middle finger 3 can be compared to the expected values for a normal hand. A preferred method of analyzing the palm comprises calculating the location of each finger base to separate the fingers from the palm to isolate the palm for measurement, including area, width at widest point, height at highest point and other measurements. [1030].

Figure 11:
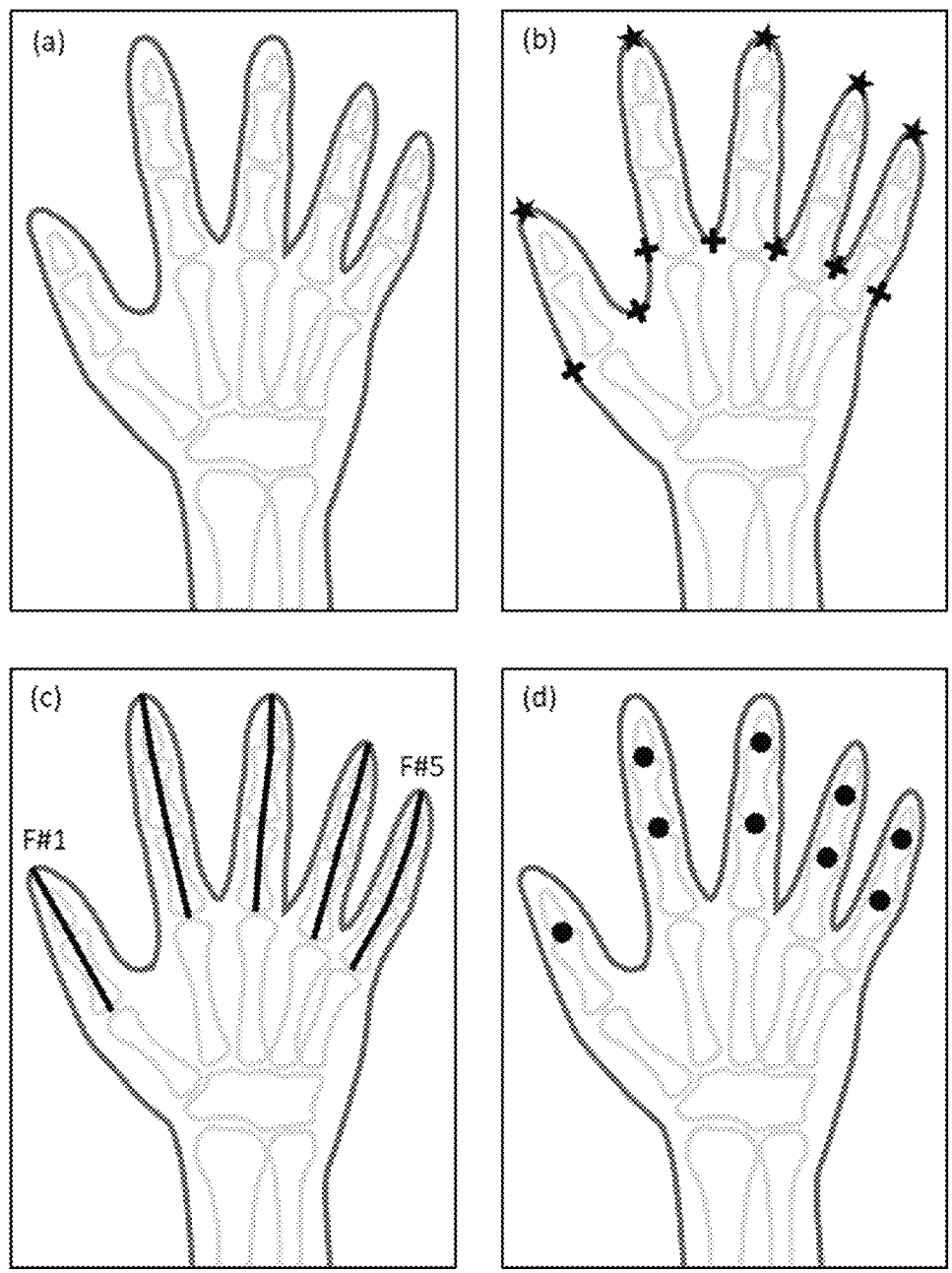
FIG. 11(a)-(d) shows exemplary images of labeled finger boundaries, fingertips, finger vertices, finger centerlines and finger thickness.

FIG. 11a illustrates an image of a hand with the detected boundary overlay. FIG. 11b illustrates an image of a hand with labeled fingertips and vertices extracted from boundary information. FIG. 11c illustrates an image of a hand with labeled finger centerlines and finger boundary coordinates. FIG. 11d illustrates an image of a hand with labeled finger joint coordinates.

The method further comprises collecting the locations of the fiduciary points and the measurements of anatomical features determined using the method as a data set that can be compared from time to time to determine changes in the anatomy of the hand that may indicate disease progression, healing or other changes that may be diagnostically useful. The method can further comprise collecting sensor information from the smartphone comprising at least one of geographic location, time and date, ambient light levels, smartphone camera settings and characteristics and correlating these with the measurements as part of the data set. The method can further comprise correlating the geographic location and time and date with external databases containing weather data, population statistics such as mortality, disease incidence and similar measures and correlating them with the image analysis. The method can further comprise collecting biographic information from the subject comprising at least one of age, gender, disease status, pain status, medication status, medical history or other useful biographic variables and correlating them with the image analysis.

While the foregoing description of the methods is directed to imaging of the hand for diagnosis and monitoring of hand arthritis and other diseases, it is obvious for one skilled in the art that the method is equally applicable to diagnosis and monitoring other human anatomy such as the foot, the arms, the legs, and as well as the whole body. In the case of images of the whole body, where the paper reference object may be too small, a substitute reference object such as a door or wall poster of known dimensions may be used as the reference object. In some embodiments of the invention, other reference objects may be preferred, including smaller cards, business cards or coins or paper currency or other useful objects.

FIG. 12 shows an embodiment of the invention applied in which an arm showing symptoms of the skin diseases psoriasis is imaged. Following image capture and the spatial calibration of the image according to the dimensions of the reference background object, an image segmentation algorithm is applied to the image of the arm to separate areas showing psoriasis from areas that do not. Suitable methods are similar to those applied to the hand and previously described above. Suitable segmentation algorithms include but are not limited to thresholding, k-means clustering, and k-means clustering applied to following transformation in color space, for example from RGB color space to L*a*b color space. FIG. 12a shows a black and white representation of a color image of the arm with psoriasis following spatial calibration and correction by image warping. FIG. 12b shows the binary image produced by the image segmentation algorithm that separates the psoriatic regions from the normal skin of the arm. FIG. 12c shows an image where boundary detection applied to the binary segmented image is overlaid on the color image of the arm with the psoriatic region. From this information various features can be measured related to the areas affected by psoriasis. These can include color, texture, area affected and other similar measures, including those measures described above for the hand and other anatomical regions.

While the description of the methods describe above refer to analysis of two dimensional images it is also obvious that the method is not limited to two dimensional images but may be applied to three-dimensional images such as those captured using magnetic resonance imaging laser scanning tomography, multi-angle imaging reconstruction or any other method of creating a three dimensional image of an object. In this case where a three dimensional object is used the boundary of the hand would no longer be a two dimensional linear array of pixels, but a three dimensional surface comprised of voxels.

The invention claimed is:

1. A system for assessment and monitoring of joint abnormalities in a subject caused by disease or injury, wherein said system captures and analyzes an image of an affected anatomical region of said subject where one or more joints are located, said system comprising:
    (a) a mobile device comprising a camera for capturing a digital image of said affected anatomical region and a reference object of known dimensions positionable in a background relative to said affected anatomical region;
    (b) a mobile application executable by said mobile device and configured to collect sensor data relating to said digital image; and
    (c) processing software executable by a processor and configured to analyze said sensor data to determine anatomical measurements of said affected anatomical region relevant to said assessment and monitoring of joint abnormalities, said measurements comprising the dimensions of said one or more joints and the amount of angular deviation of anatomical structures at said one or more joints;
    wherein said amount of angular deviation of anatomical structures at said one or more joints comprises the amount of deviation between measurements of one or more of said anatomical structures in said subject having said joint abnormalities and expected values for said anatomical structures in an individual having normal anatomy.

2. The system as defined in claim 1, wherein said subject is a human being, said affected anatomical region is a hand or foot of said subject, and said joint abnormalities are caused by arthritis.

3. The system as defined in claim 1, wherein said mobile device is a smartphone or tablet computer.

4. The system as defined in claim 3, wherein said mobile device has Internet connectivity and wherein said processor is a cloud processing server.

5. The system as defined in claim 1, wherein said sensor data comprises at least one of image data, camera data, ambient light sensor data, orientation sensor data, geographic location data, and time and date data.

6. The system as defined in claim 1, wherein at least one of said mobile application and said processing software is configured to determine whether image capture conditions of said digital image are acceptable for further processing of said digital image.

7. The system as defined in claim 1, wherein said mobile application is configured to provide an interface enabling a user of said mobile device to input biographical and environmental data relevant to said subject, wherein said biographical and environmental data comprises at least one of biographical information, experiential measures of pain and movement, medication use, weather and regional demographics.

8. The system as defined in claim 7, comprising electronic health record software executable on a cloud database server for storing and retrieving said anatomical measurements and said biographical and environmental data specific to said subject.

9. The system as defined in claim 1, wherein said processing software is configured to produce a report indicating the condition of said one or more joints based on said anatomical measurements.

10. The system as defined in claim 4, comprising a cloud database server operable to store and retrieve reference measurements, wherein said processing software is configured to compare said anatomical measurements to said reference measurements.

11. The system as defined in claim 4 wherein said processing software executable on said cloud processing server is configured to perform operations to determine said anatomical measurements, said operations comprising:
 (a) analyzing said sensor data to make adjustments to said digital image, wherein said adjustments comprise correcting a distortion of said image selected from the group consisting of a spatial distortion, a color balance distortion, and a perspective distortion;
 (b) segmenting a calibrated image of said affected anatomical region from a background of said digital image to provide a segmented image;
 (c) determining a boundary of said affected anatomical region and anatomical fiduciary points in said segmented image; and
 (d) calculating said anatomical measurements based on said boundary and said fiduciary points.

12. A method for assessment and monitoring of joint abnormalities in a subject caused by disease or injury, comprising:
 (a) capturing a digital image of an affected anatomical region of said subject where one or more joints are located and a reference object of known dimensions positionable in a background relative to said affected anatomical region, wherein said image is captured using a mobile device comprising a camera;
 (b) collecting sensor data from said mobile device relating to said digital image; and
 (c) analyzing said sensor data to determine anatomical measurements of said affected anatomical region relevant to said assessment and monitoring of joint abnormalities, said measurements comprising the dimensions of said one or more joints and the amount of angular deviation of anatomical structures at said one or more joints;
 wherein said amount of angular deviation of anatomical structures at said one or more joints comprises the amount of deviation between measurements of one or more of said anatomical structures in said subject having said joint abnormalities and expected values for said anatomical structures in an individual having normal anatomy.

13. The method of claim 12, wherein said subject is a human being, said affected anatomical region is a hand or foot of said subject, and wherein said joint abnormalities are caused by arthritis.

14. The method of claim 12, wherein said mobile device is a smartphone or tablet computer and wherein said method comprises transmitting said sensor data from said mobile device to a cloud processing server.

15. The method as defined in claim 12, wherein said sensor data comprises at least one of image data, camera data, ambient light sensor data, orientation sensor data, geographic location data, and time and date data.

16. The method as defined in claim 12, comprising determining, prior to analyzing said sensor data to determine said anatomical measurements, whether image capture conditions of said digital image are acceptable for further processing, and, if not, capturing a replacement digital image of said affected anatomical region and said reference object.

17. The method as defined in claim 12, comprising collecting biographical and environmental data relevant to said subject using said mobile device, wherein said biographical and environmental data comprises at least one of biographical information, experiential measures of pain and movement, medication use, weather and regional demographics.

18. The method as defined in claim 17, comprising providing a cloud database server for storing and retrieving an electronic health record specific to said subject comprising said anatomical measurements and said biographical and environmental data.

19. The method as defined in claim 12, comprising providing a report indicating the condition of said one or more joints based on said anatomical measurements.

20. The method as defined in claim 12, comprising comparing said anatomical measurements to reference measurements.

21. The method as defined in claim 20, wherein said reference measurements are prior measurements of said one or more joints of said subject, wherein said comparing enables monitoring of any changes to said one or more joints over time.

22. The method as defined in claim 17, comprising comparing said anatomical measurements and said biographical and environmental data to historical reference data, wherein said historical reference data comprises prior anatomical measurements and biographical and environmental data specific to said subject, wherein said comparing enables monitoring of any changes to said one or more joints relative to any changes to said biographical and environmental data over time.

23. The method as defined in claim 22, wherein said monitoring provides a measure of any correlations between said changes to said one or more joints and biographical or environmental factors, wherein said factors are selected from the group consisting of treatment received by said subject, medication received by said subject, physical activity of said subject, geographic location of said subject and weather conditions at said geographic location of said subject.

24. The method as defined in claim 12, wherein said analyzing comprises:
 (a) analyzing said sensor data to make adjustments to said digital image, wherein said adjustments comprise correcting a distortion of said image selected from the group consisting of a spatial distortion, a color balance distortion, and a perspective distortion;

(b) segmenting a calibrated image of said affected anatomical region from a background of said digital image to provide a segmented image;

(c) determining in said segmented image a boundary of said affected anatomical region and anatomical fiduciary points within said boundary; and (d) calculating said anatomical measurements based on said boundary and said fiduciary points.

25. The method as defined in claim 24, wherein said perspective distortion is corrected by determining the angle of said camera relative to said affected anatomical region and said reference object when said image is captured and adjusting said image to correct said perspective distortion.

26. The method as defined in claim 24, wherein said spatial distortion is corrected by measuring the size and/or shape of said reference object in said image to determine spatial measurements of said object, comparing said spatial measurements to known values for said object, and adjusting said image to correct said spatial distortion.

27. The method as defined in claim 24, wherein said color balance distortion is corrected by measuring the color of said reference object to determine color measurements, comparing said color measurements to known values for said object, and adjusting said image to correct said color distortion.

28. The method as defined in claim 24, wherein said segmenting comprises using K-means clustering of chrominance information for said image to segment pixels corresponding to said affected anatomical region from background image data.

29. The method of claim 12, wherein said reference object is a paper sheet of known dimensions and color.

30. The method of claim 16, wherein said determining whether said image capture conditions of said digital image are acceptable comprises analyzing said orientation sensor data to determine whether the orientation of said camera relative to said affected anatomical region is at a desirable angle.

31. The method of claim 16, wherein said determining whether image capture conditions of said digital image are acceptable comprises analyzing said ambient light sensor data to determine whether illumination of said affected anatomical region is suitable.

32. The method of claim 16, wherein said determining whether image capture conditions of said digital image are acceptable comprises determining if said reference object is within the field of view.

33. The method of claim 24, wherein said affected anatomical region is a hand and wherein said calculating said anatomical measurements comprises determining the length and location of segments of a finger extending between said one or more joints and determining the relative angle of said segments, wherein determining said relative angle provides a measure of joint breakdown causing deviation of said segments away from an anatomically normal orientation.

34. A system for assessment and monitoring of joint abnormalities in a subject caused by disease or injury, wherein said system captures and analyzes an image of an affected anatomical region of said subject where one or more joints are located, said system comprising:

(a) a mobile device comprising a camera for capturing a digital image of said affected anatomical region and a reference object of known dimensions positioned in a background independently of said affected anatomical region;

(b) a mobile application executable by said mobile device and configured to collect sensor data relating to said digital image; and (c) processing software executable by a processor and configured to analyze said sensor data to determine anatomical measurements of said affected anatomical region relevant to said assessment and monitoring of joint abnormalities, said measurements comprising the dimensions of said one or more joints and the amount of angular deviation of anatomical structures at said one or more joints;

wherein said amount of angular deviation of anatomical structures at said one or more joints comprises the amount of deviation between measurements of one or more of said anatomical structures in said subject having said joint abnormalities and expected values for said anatomical structures in an individual having normal anatomy.

* * * * *